(12) United States Patent
Spaner

(10) Patent No.: US 6,258,357 B1
(45) Date of Patent: Jul. 10, 2001

(54) INHIBITION OF GRAFT VERSUS HOST DISEASE

(75) Inventor: David Elliot Spaner, Toronto (CA)

(73) Assignee: Vasogen Ireland Limited, Shannon (IE)

( * ) Notice: Subject to any disclaimer, the term of this patent is extended or adjusted under 35 U.S.C. 154(b) by 0 days.

(21) Appl. No.: 09/363,678

(22) Filed: Jul. 30, 1999

(30) Foreign Application Priority Data

Jul. 30, 1998 (CA) .................................................. 2244554

(51) Int. Cl.[7] .......................... A01N 63/00; A61K 45/00; A61K 47/00; A61K 39/00; A61L 2/00
(52) U.S. Cl. .................................... 424/93.71; 424/278.1; 424/613; 424/810; 422/24
(58) Field of Search .............................. 424/93.71, 278.1, 424/613, 810; 422/24

(56) References Cited

U.S. PATENT DOCUMENTS 5,980,954 * 11/1999 Bolton .

FOREIGN PATENT DOCUMENTS

96/37208 11/1996 (WO) .
98/07436 2/1998 (WO) .

OTHER PUBLICATIONS

Spaner et al. Abstract 4272, Blood Nov. 15, 1998.

* cited by examiner

Primary Examiner—Patrick J. Nolan
Assistant Examiner—Gerald R. Ewoldt
(74) Attorney, Agent, or Firm—Burns, Doane, Swecker & Mathis, LLP

(57) ABSTRACT

The development of graft versus host disease in a mammalian patient undergoing cell transplantation therapy for treatment of a bone marrow mediated disease, is prevented or alleviated by subjecting at least the T-cells of the allogeneic cell transplantation composition, extracorporeally, to oxidative stress, in appropriate dosage amounts, such as bubbling a gaseous mixture of ozone and oxygen through a suspension of the T-cells. The process may also include irradiation of the cells with UV light, simultaneously with the application of the oxidative stress. The oxidative stress induces reduced inflammatory cytokine production and a reduced proliferative response in the T-cells.

7 Claims, 2 Drawing Sheets

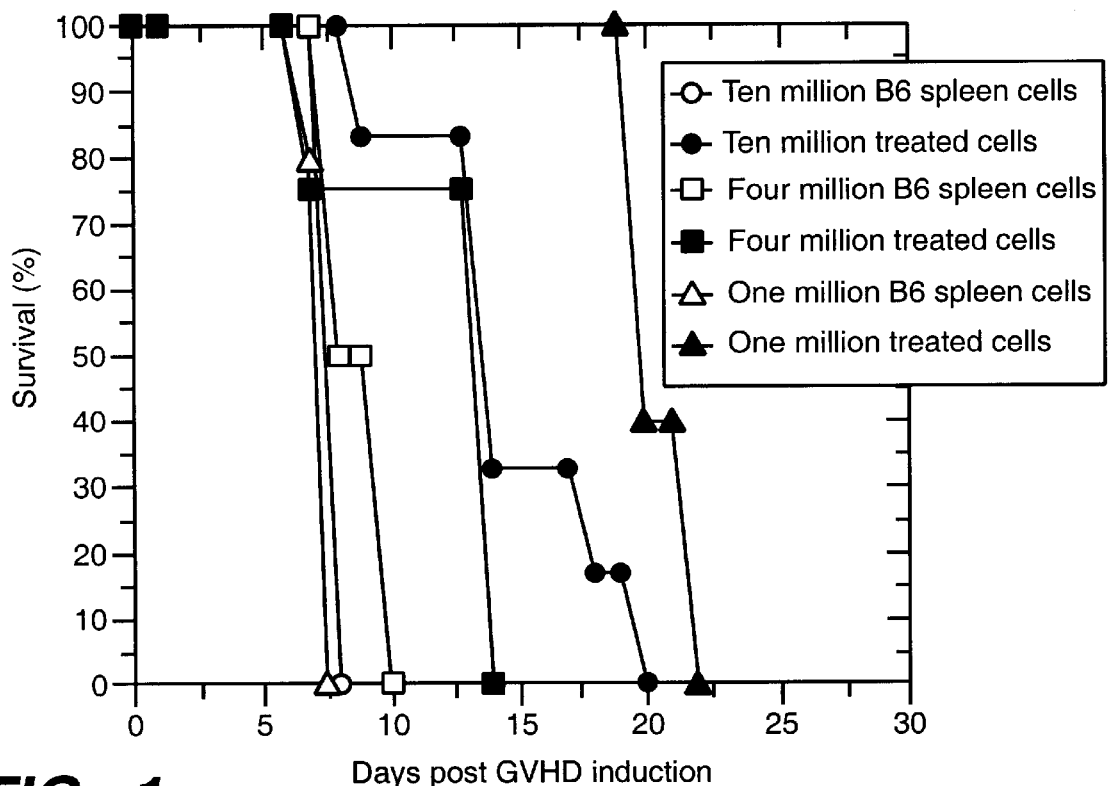
FIG._1
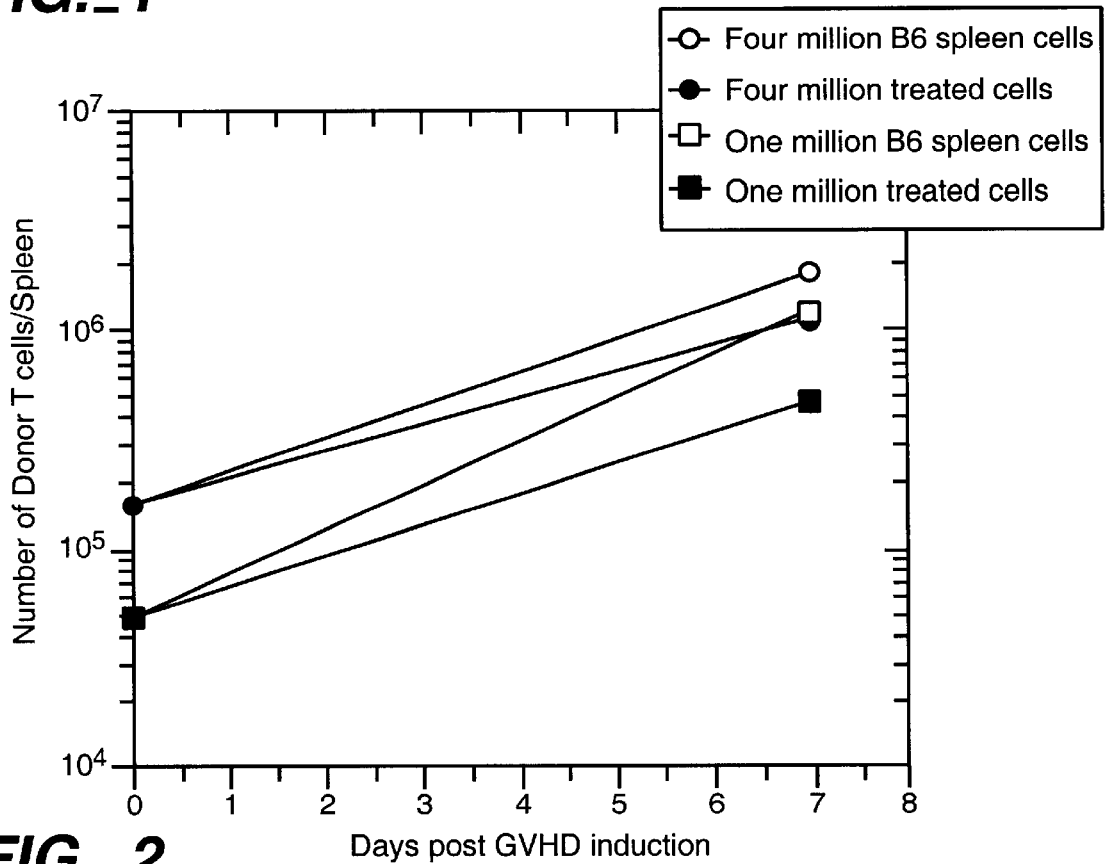
FIG._2

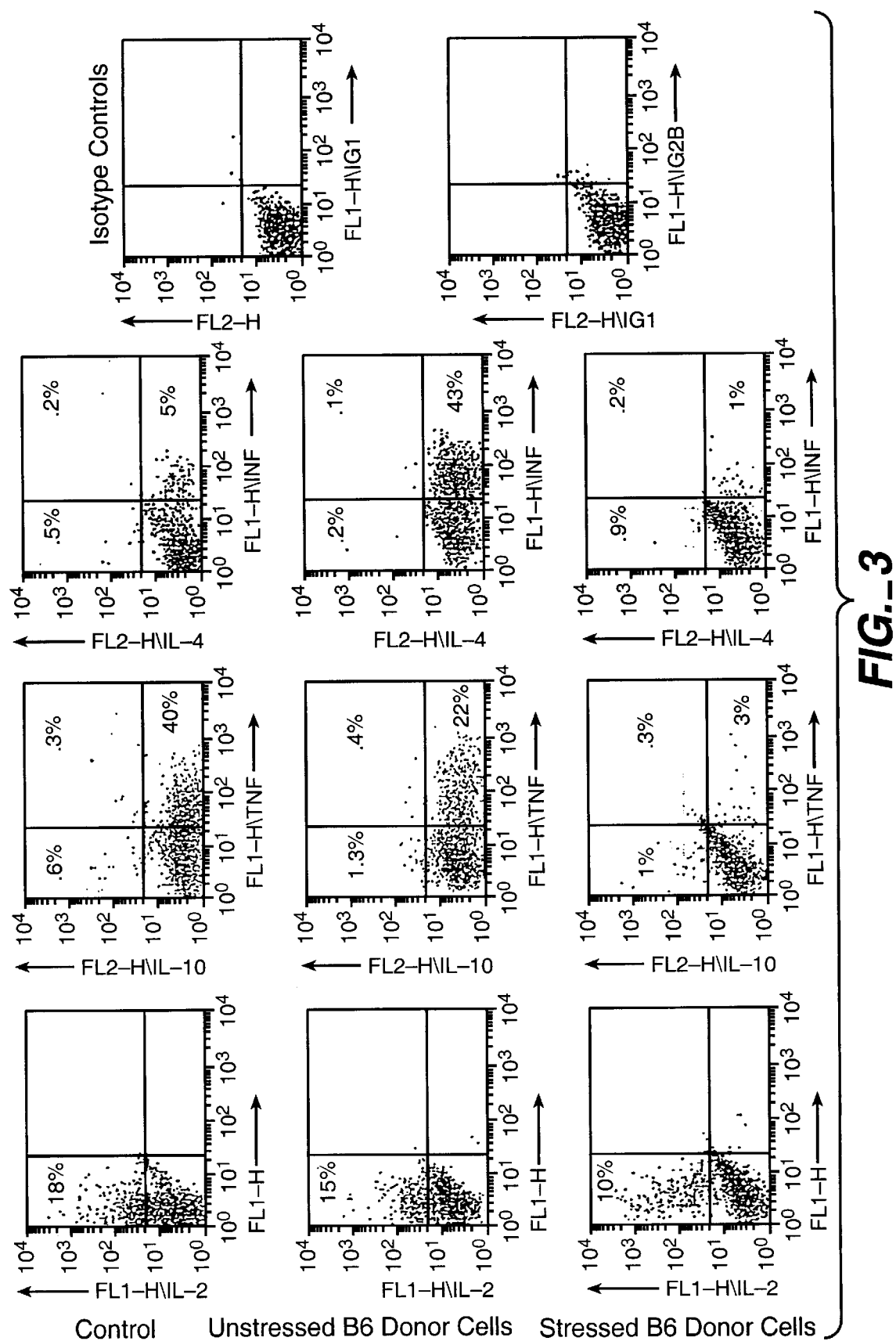
FIG._3

US 6,258,357 B1

INHIBITION OF GRAFT VERSUS HOST DISEASE

FIELD OF THE INVENTION

This invention relates to cellular compositions useful in medical treatments, processes for their preparation and their uses in medical treatments. More specifically, it relates to cellular compositions useful in alleviation of complications following allogeneic bone marrow transplantation, namely graft versus host disease in mammalian patients, especially in human patients, and to processes for preparation of such compositions of matter.

BACKGROUND OF THE INVENTION

Bone marrow transplantation, BMT, is indicated following a process which destroys bone marrow. For example, following intensive systemic radiation or chemotherapy, bone marrow is the first target to fail. Metastatic cancers are commonly treated with very intensive chemotherapy, which is intended to destroy the cancer, but also effectively destroys the bone marrow. This induces a need for BMT. Leukemia is a bone marrow malignancy, which is often treated with BMT after chemotherapy and/or radiation has been utilized to eradicate malignant cells. BMT is currently used for treatment of leukemias which are life-threatening. Some autoimmune diseases may be severe enough to require obliteration of their native immune systems which includes concomitant bone marrow obliteration and requires subsequent bone marrow transplantation. Alleviation of any but the most acute life-threatening conditions involving bone marrow disorders with BMT is, however, generally regarded as too risky, because of the likelihood of the onset of graft versus host disease.

Graft-versus-host disease, GVHD, is an immunological disorder that is the major factor that limits the success and availability of allogeneic bone marrow or stem cell transplantation (collective referred to herein as allo-BMT) for treating some forms of otherwise incurable hematological malignancies, such as leukemia. GVHD is a systemic inflammatory reaction which causes chronic illness and may lead to death of the host mammal. At present, allogeneic transplants invariably run a severe risk of associated GVHD, even where the donor has a high degree of histocompatibility with the host.

GVHD is caused by donor T-cells reacting against systemically distributed incompatible host antigens, causing powerful inflammation. In GVHD, mature donor T-cells that recognize differences between donor and host become systemically activated. Current methods to prevent and treat GVHD involve administration of drugs such as cyclosporin-A and corticosteroids. These have serious side effects, must be given for prolonged periods of time, and are expensive to administer and to monitor. Attempts have also been made to use T-cell depletion to prevent GVHD, but this requires sophisticated and expensive facilities and expertise. Too great a degree of T-cell depletion leads to serious problems of failure of engraftment of bone marrow stem cells, failure of hematopoietic reconstitution, infections, or relapse. More limited T-cell depletion leaves behind cells that are still competent to initiate GVHD. As a result, current methods of treating GVHD are only successful in limited donor and host combinations, so that many patients cannot be offered potentially life-saving treatment.

BRIEF REFERENCE TO THE PRIOR ART

International Patent Application No. PCT/CA97/00564 Bolton describes an autovaccine for alleviating the symptoms of an autoimmune disease in a mammalian patient, comprising an aliquot of modified blood obtained from the same patient and treated extracorporeally with ultraviolet radiation and an oxygen/ozone gas mixture bubbled therethrough, at an elevated temperature (42.5° C.), the autovaccine being re-administered to the same patient after having been so treated.

It is an object of the present invention to provide a process of alleviating the development of GVHD complications in a mammalian patient undergoing allo-BMT procedures.

SUMMARY OF THE INVENTION

According to the present invention, a patient being treated by allo-BMT is administered a composition containing T-cells obtained from an allogeneic donor, said T-cells having been subjected in vitro to oxidative stress to induce therein decreased inflammatory cytokine production coupled with reduced proliferative response. It appears that such oxidatively stressed allogeneic T-cells when injected into a mammalian patient, have a down-regulated immune response and a down-regulated destructive allogeneic response against the recipient, so that engraftment of the hematopoietic stem cells, administered along with or separately from the stressed T-cells, can take effect with significantly reduced risk of development of GVHD. The population of stressed T-cells nevertheless appears to be able to exert a sufficient protective effect on the mammalian system to guard against failure of engraftment and against infection, whilst the hematopoietic system is undergoing reconstitution, at least in part, by proliferation and differentiation of the allogeneic stem cells.

One aspect of the present invention provides, accordingly, a process of treating a mammalian patient for alleviation of a bone marrow mediated disease, with alleviation of consequently developed graft versus host disease (GVHD), which comprises administering to the patient allogeneic hematopoietic stem cells and allogeneic T-cells, at least a portion of said T-cells having been subjected to oxidative stress in vitro, prior to administration to the patient, so as to induce an altered cytokine production profile and a reduced proliferative response therein.

Another aspect of the present invention provides a population of mammalian T-cells, essentially free of stem cells, said T-cells having been subjected in vitro to oxidative stress so as to induce in said cells an altered cytokine production profile and a reduced proliferative response.

A further aspect of the present invention provides a process for preparing an allogeneic cell population for administration to a human patient suffering from a bone marrow mediated disease, which comprises subjecting, in vitro, a population of donor cells enriched in T-cells to oxidative stress to induce in said T-cells an altered cytokine production profile and a reduced proliferative response.

BRIEF REFERENCE TO THE DRAWINGS

FIGS. 1 and 2 of the accompanying drawings are graphical presentations of results obtained according to Example 3 below.

FIG. 3 is a depiction of the results obtained from Example 4 below.

DESCRIPTION OF THE PREFERRED EMBODIMENTS

The process of the present invention involves an initial collection of hematopoietic stem cells and T-cells from a donor. The preferred source of such cells is mobilized stem cells and T-cells from the peripheral blood of the donor. Stem cells are present in very small quantities in peripheral blood, and one preferred way of operating in accordance with the invention is to enrich the stem cell population of the donor's peripheral blood, and then to extract the donor's peripheral blood for use as a source of stem cells and T-cells for treatment as described and subsequent injection into the patient. Enrichment may be achieved by giving the donor a course of injections of appropriate growth factors, over several days e.g. five days prior to extracting peripheral blood from the donor. Appropriate cell fractions can be collected from the blood by leukopheresis, a known procedure, as it is extracted, with the plasma and red cells being returned to the donor, in a closed flow system. The white cell collection, which contains the stem cells (about 3%) and T-cells (about 40%) along with B-cells, neutrophils and other white cells, may be treated to alter their cytokine production profiles and to reduce the proliferative response of the T-cells therein, and then administered to the host patient, in accordance with the invention, as a whole collection of cells (peripheral blood mononuclear cells). Preferably, however, the donor T-cells are separated from the other cells, so that only the T-cells are subjected to oxidative stress and then administered to the patient, with the stem cells for engraftment being administered to the patient separately from the treated T-cells. For practical purposes, however, subjection of the collection of peripheral blood mononuclear cells to the stressors is satisfactory, without further fractionation to isolate the T-cells, which is a difficult and expensive procedure. Separate administration of stem cells is strongly preferred.

If for some reason it is desired to subject the entire white cell collection to oxidative stress to induce the aforementioned changes in the T-cell portion thereof, and then administer the entire collection to the patient, it is preferred to protect the stem cells from any damaging effects of the oxidative stress in a manner described below.

In an alternative, but less preferred, procedure, whole bone marrow of the donor can be used as the source of T-cells and stem cells for the process of the invention. Whole bone marrow has in the past been the usual source of cells for allogeneic cell transplantation procedures, and can indeed be used in the present process. It is however an inconvenient and uncomfortable procedure for the donor, requiring anaesthetic and lengthy extraction procedures. Any source of T-cells and stem cells from the donor can be used in principle, but peripheral blood enriched in stem cells and T-cells is the most clinically convenient.

The alteration in cytokine production profile induced in the T-cells in the process of the invention is preferably a reduction in production of inflammatory cytokines, such as interferon-γ and tissue necrosis factor-α.

The oxidative stress may be applied to the T-cells by subjecting them to an oxidative environment such as the addition of a gaseous, liquid or solid chemical oxidizing agent (ozone, molecular oxygen, ozone/oxygen gas mixtures, permanganates, periodates, peroxides, drugs acting on biological systems through an oxidative mechanism such as adriamycin, and the like). In one preferred method according to the invention, the T-cells are subjected, in suspension, to a gaseous oxidizing agent, such as an ozone/oxygen gas mixture bubbled through the suspension of cells, optionally in combination with the simultaneous subjection of the cells to ultraviolet radiation, in appropriate doses.

One method according to the present invention subjects the allogeneic white cells from the donor, including both the stem cells and the T-cells, to oxidative stress. This eliminates the need to include a complicated and costly step of separating the T-cells from the other cellular components of the white cells composition. In such case, however, it is strongly preferred to protect the stem cells in the composition from deleterious effects of the stress. This can be accomplished by including one or more stem cell growth factors in the cell composition at the time of subjecting it to the stress. Protection of the stem cells from the deleterious effects of the oxidative stress is achieved by the presence of growth factors, and so, prior to subjecting the stem cell-T-cell composition to oxidative stress, one or more stem cell growth factors are added to the composition. Stem cell growth factors useful in the process are cytokines which promote survival of stem cells (but not T-cells) during this stressing. They are cytokines which interact with growth receptors on stem cells. They are believed to activate the MAP-kinase pathway of the cell, resulting in the activation of erk. Examples of suitable such growth factors, include stem cell specific growth factors, kit-ligand, IL-3, GM-CSF and FLT 3 ligand, all of which are known. It is preferred to add precise amounts of extracted, purified growth factors or, especially, recombinant growth factors available on the market, or combinations thereof, suitably dissolved or suspended in appropriate, biologically acceptable fluids.

One preferred method of subjecting the allogeneic T-cells to oxidative stress according to the invention involves exposing a suspension of the cells to a mixture of medical grade oxygen and ozone gas, for example by bubbling through the suspension a stream of medical grade oxygen gas having ozone as a minor component therein. The suspending medium may be any of the commonly used biologically acceptable media which maintains cells in viable condition. The ozone gas may be provided by any conventional source known in the art. Suitably the gas stream has an ozone content of from about 1.0–100 µg/ml, preferably 3–70 µg/ml and most preferably from about 5–50 µg/ml. The gas stream is supplied to the aliquot at a rate of from about 0.01–2 liters per minute, preferably 0.05–1.0 liters per minute, and most preferably at about 0.06–0.30 liters per minute (STP).

Another method of subjecting the T-cells to oxidative stress to render them suitable for use in the present invention is to add to a suspension of the cells a chemical oxidant of appropriate biological acceptability, and in biologically acceptable amounts. Permanganates, periodates and peroxides are suitable, when used in appropriate quantities. Hydrogen peroxide is useful in demonstrating the effectiveness of the process of the invention and in giving guidance on the appropriate quantity of oxidizing agent to be used, although it is not an agent of first choice for the present invention, for practical reasons. Thus, a suitable amount of oxidizing agent is hydrogen peroxide in a concentration of from 1 micromolar–2 millimolar, contacting a 10 ml suspension containing from $10^{-6}$ to $10^{-8}$ cells per ml, for 20 minutes, or equivalent oxidative stress derived from a different oxidizing agent. Optimum is about 1 millimolar hydrogen peroxide in such a suspension for about 20 minutes, or the equivalent of another oxidizing agent calculated to give a corresponding degree of oxidative stress to the cells.

The size of the cell suspension to be subjected to oxidative stress is generally from about 0.1 ml to about 1000 ml, preferably from about 1–500, and containing appropriate numbers of T-cells for subsequent administration to a patient undergoing allo-BMT. These numbers generally correspond to those used in prior methods of allogeneic T-cell administration in connection with allo-BMT, and are familiar to those skilled in the art.

One specific process according to the invention is to subject the cell suspension simultaneously to oxygen/ozone bubbled through the suspension and ultraviolet radiation. This also effects the appropriate changes in the nature of the T-cells. Care must be taken not to utilize an excessive dosage of oxygen/ozone or UV, to the extent that the cell membranes are caused to be disrupted, or other irreversible damage is caused to an excessive number of the cells.

The temperature at which the T-cell suspension is subjected to the oxidative stress does not appear to be critical, provided that it keeps the suspension in the liquid phase and is not so high that it causes cell membrane disruption. The temperature should not be higher than about 45° C.

When ultraviolet radiation is used in conjunction with the oxygen/ozone oxidative stressor, it is suitably applied by irradiating the suspension under treatment from an appropriate source of UV radiation, while the aliquot is maintained at the aforementioned temperature and while the oxygen/ozone gaseous mixture is being bubbled through the aliquot. The ultraviolet radiation may be provided by any conventional source known in the art, for example by a plurality of low-pressure ultraviolet lamps. There is preferably used a standard UV-C source of ultraviolet radiation, namely UV lamps emitting primarily in the C-band wavelengths, i.e. at wavelengths shorter than about 280 nm. Ultraviolet radiation corresponding to standard UV-A and UV-B sources can also be used. Preferably employed are low-pressure ultraviolet lamps that generate a line spectrum wherein at least 90% of the radiation has a wavelength of about 254 nm. An appropriate dosage of such UV radiation, applied simultaneously with the aforementioned temperature and oxidative environment stressors, is obtained from lamps with a power output of from about 5 to about 25 watts, preferably about 5 to about 10 watts, at the chosen UV wavelength, arranged to surround the sample container holding the aliquot. Each such lamp provides an intensity, at a distance of 1 meter, of from about 40–80 micro watts per square centimeter. Several such samples surrounding the sample container, with a combined output at about 254 nm of 15–40 watts, preferably 20–40 watts, operated at maximum intensity may advantageously be used. At the incident surface of the aliquot, the UV energy supplied may be from about 0.25–4.5 j/cm$^2$ during a 3-minute exposure, preferably 0.9–1.8 j/cm$^2$. Such a treatment provides a suspension aliquot which is appropriately modified according to the invention ready for injection into the patient.

The time for which the aliquot is subjected to the stressors can be from a few seconds to about 60 minutes. It is normally within the time range of from about 0.5–60 minutes. This depends to some extent upon the chosen intensity of the UV irradiation, the temperature and the concentration of and rate at which the oxidizing agent is supplied to the aliquot. Some experimentation to establish optimum times and dosages may be necessary on the part of the operator, once the other stressor levels have been set. Under most stressor conditions, preferred times will be in the approximate range of about 0.5–10 minutes, most preferably 2–5 minutes, and normally around 3 minutes.

In the practice of one preferred process of the present invention, the suspension of cells may be treated with oxygen/ozone gas mixture and optionally also with UV radiation using an apparatus of the type described in U.S. Pat. No. 4,968,483 Mueller. The suspension is placed in a suitable, sterile, UV-radiation-transmissive container, which is then fitted into the machine. The temperature of the aliquot is adjusted to the predetermined value, e.g. 42.5±1° C., by the use of a suitable heat source such as an IR lamp, and the UV lamps are switched on for a fixed period before the gas flow is applied to the aliquot providing the oxidative stress, to allow the output of the UV lamps to stabilize. The oxygen/ozone gas mixture, of known composition and control flow rate, is applied to the aliquot, for the predetermined duration of 0.5–60 minutes, preferably 1–5 minutes and most preferably about 3 minutes as discussed above. In this way, the suspension is appropriately modified according to the present invention sufficient to achieve the desired effects of alleviation or prevention of GVHD.

From another aspect, the preferred embodiment of the present invention may be viewed as a process of treating allogeneic T-cells prior to their introduction into a patient, by extracorporeally stressing the T-cells, which comprises subjecting the T-cells to oxidative stress such as exposure to ozone or ozone/oxygen. The treated allogeneic T-cells from the process of the invention have a direct effect on the development and progression of GVHD. The donor T-cells pretreated according to the process of the invention prior to introduction into the host patient, have been modified, so that they no longer mount a deleterious response. Their ability to mount an inflammatory cytokine response has been decreased. For example their ability to secrete IFNγ, TNFα and IL-2, and their proliferative response to standard mitogens has been reduced. Accordingly they no longer react against incompatible systemically distributed host histocompatibility antigens to cause inflammation to any great extent. The allogeneic stem cells administered to the patient can proceed with engraftment with improved chance of success. After a period of time, the treated T-cells largely recover their proliferative ability and immune response functions, but remain relatively unresponsive (tolerant) to differing host histocompatibility antigens.

The invention is further described, for illustrative purposes, in the following specific examples.

SPECIFIC DESCRIPTION OF THE MOST PREFERRED EMBODIMENTS

The spleen of a mammal offers a convenient, accessible source of cells, especially T-cells but also including small quantities of stem cells and is particularly useful in connection with animal models for experimental purposes.

Experimental testing to obtain indication of the utility of the process of the present invention was conducted using a model of acute GVHD in SCID mice. T-cells from C57B1/6J (B6) mice were intravenously injected into sub-lethally irradiated CB-17 SCID mice. The latter are congenitally lymphopenic and provide a strong stimulus for donor cells due to their complete disparity at the major histocompatibility locus (MHC). The mean survival time of host mice in this model is 14 days. GVHD is characterized by suppression of host hematopoietic recovery from irradiation; expansion of T-cells that use Vβ3 chain to form their T-cell receptor complexes (TCR's); spontaneous secretion of interferon-γ and TNF-α, by donor T-cells, and aberrant localization of donor T-cells to the red pulp areas of the spleen. If donor marrow is co-injected with T-cells, a chronic form of GVHD results.

EXAMPLE 1

Mouse spleen cells from C57B1/6J (B6) mice were suspended to a density of $10^7$/ml in α-MEM, 2ME and 10% fetal calf serum (FCS). The FCS contains cytokines and growth factors. The cell suspension was subjected simultaneously to ultraviolet radiation from UV-C lamps, wavelength 253.7 nm, whilst bubbling through the suspension a gas mixture of 14–15 mcg/ml ozone/medical grade oxygen, at 42.5° C. The treatment took place for 3 minutes.

Immediately after the treatment, the cells had a viability of only about 10%.

EXAMPLE 2

The experiment of Example 1 was essentially repeated except that the cells were suspended in 100% FCS. The immediate survival of the cells in this case was 50–60%, indicating that factors present in the FCS have exerted a protective effect on at least some of the cells.

EXAMPLE 3

Murine B6 spleen cells suspended in 100% FCS were subjected to UV-oxidation-heat treatment. The cell suspension was subjected simultaneously to ultraviolet radiation from UV-C lamps, wavelength 253.7 nm, whilst bubbling through the suspension a gas mixture of 14–15 mcg/ml ozone/medical grade oxygen, at 42.5° C. The treatment took place for 3 minutes. Varying numbers were injected into sub-lethally irradiated CB-17 SCID mice. Their subsequent behaviour was compared with similar numbers of B6 spleen cells, not subjected to the treatment.

FIG. 1 is a graphical presentation of the results of these experiments, where the % survival of the animals in each group is plotted as ordinate against days following injection of the treated or untreated cells. At all dosage levels, there is a marked improvement of survival when the treated cells are used as opposed to the untreated cells, demonstrating potential for the process of the invention in alleviating GVHD.

FIG. 2 of the accompanying drawings is a plot of the number of donor T-cells per spleen against days after GVHD induction, in these same experiments. This shows that the treated donor T-cells survive and expand in number in the host mice, although to a more limited degree than control, untreated B6 T-cells.

EXAMPLE 4

Six days after initiation of GVHD in the mice by injection of the donor cells (treated and untreated), donor T-cells were separated from SCID spleen cells by density gradient centrifugation. Intracellular cytokine staining was performed according to the method of Ferrick, D. A. et. al., NATURE 373 225, 257, 1995. The staining was performed on spleen cell suspensions on day 8 after injection of B6 spleen cells. Cytokine production was determined 4 hours after stimulation in vitro with PHA and ionomycin in the presence of brefeldin-A and after gating on $CD4^+$ and $CD8^+$. The results were assessed by intracellular flow cytometry, and the results thereof are depicted in FIG. 3 of the accompanying drawings. The percentage of each cells in each quadrant is recorded. The drawing shows significantly reduced levels of the inflammatory cytokines interferon-γ (INF) and tissue necrosis factor-α (TNF), lower right quadrants, from the T-cells which had been stressed as described in Example 1, as compared with untreated cells and controls.

EXAMPLE 5

Inversion of the normal ratio of CD4+ to CD8+ T-cells (usually approximately 2:1) is known to accompany GVHD. By intracellular cytokine staining techniques following the method of Ferrick et.al., *Nature* 373: 255–257, 1995 and using anti-CD4 and CD8-tricolor antibodies, CD4/CD8 ratios were determined. In the untreated donor spleen cells after injection into sub-lethally irradiated mice, the inversion of the normal ratio was confirmed. The initial CD4/CD8 ratios of 1.3±0.2 and 2.2±0.3 decreased to 0.33±0.05 and 0.9±0.1 by day 13 for unstressed B6 and C3H donor T cells, respectively, at a time when many animals were succumbing to GVHD. In contrast, the ratios remained greater than 1 at all times and correlated with the lack of clinical evidence of GVHD when donor cells had been pretreated with the stressors as described in Example 1.

EXAMPLE 6

This example demonstrates the principle of the invention, using oxidative stress alone, provided by hydrogen peroxide, an effective chemical oxidizing agent and representative of many other, perhaps more biologically suitable, chemical oxidizing agents.

Peripheral human blood mononuclear cells PBMCs, which is a collection of white blood cells comprising about 40% T-cells, were stressed by contact with aqueous solutions of hydrogen peroxide, of various concentrations, for 20 minutes. Their immediate survival was measured, along with their immediate phytohaemagglutinin (PHA) response. Then their survival after 24 hours was measured, followed by their PHA response (tritiated thymidine uptake following mitogenic stimulation with PHA) and cytokine profile after 7 days. The results are given in the following table.

TABLE

| Conc. $H_2O_2$ | Immediate survival % | 24 hr survival % | Immediate PHA response | PHA response 7-day | Cytokine Profile |
|---|---|---|---|---|---|
| 100 μmole/L | 80–90 | 100 | 2000 | + | IFN↓ |
| 300 μmole/L | 80–90 | 50 | 2000 | + | IFN↓ |
| 1 mmole/L | 80–90 | 40 | 400 | + | IFN↓ |
| 3 mmole/L | 80–90 | 40 | 400 | + | IFN↓ |
| Control | 95 | 95 | 8575 | + | IFN↑ |

These results indicate that T-cells subjected to oxidative stress alone achieve a decreased proliferative response and decreased inflammatory cytokine production, suitable for use in the present invention.

I claim:

1. A process of alleviating the development of graft versus host disease complications in a mammalian patient undergoing or about to undergo a bone marrow transplant, which comprises extracting from an allogeneic human donor an aliquot of whole blood; separating from said aliquot a cellular fraction enriched in T-cells; subjecting said fraction to oxidative stress in vitro so as to induce decreased inflammatory cytokine production and a reduced proliferative response therein; and administering the oxidatively stressed fraction to the patient.

2. The process of claim 1, wherein the oxidatively stressed fraction of T-cells is administered to the patient separately from administration of stem cells from the allogeneic donor to the patient.

3. The process of claim 2, wherein the oxidatively stressed T-cell fraction consists essentially of peripheral blood mononuclear cells obtained from peripheral human blood.

4. The process of claim 2, wherein the oxidatively stressed T-cell fraction has been subjected to oxidative stress by application thereto of a gaseous oxygen/ozone mixture.

5. The process of claim 2, wherein the oxidatively stressed T-cell fraction has been subjected to oxidative stress by application thereto of a chemical oxidizing agent.

6. The process of claim 4, wherein the oxidatively stressed T-cell fraction has been additionally subjected to UV radiation, simultaneously with the subjection to oxidative stress.

7. The process of claim 5 wherein the oxidatively stressed T-cell fraction has been additionally subjected to UV radiation, simultaneously with the subjection to oxidative stress.

* * * * *